United States Patent [19]
Schulte et al.

[11] Patent Number: 5,011,934
[45] Date of Patent: Apr. 30, 1991

[54] PROCESS FOR PREPARING 1-ALKYLIMIDAZOLES

[75] Inventors: Heinz-Guenther Schulte; Jeffrey L. Narum, both of Santa Rosa; Michael R. Johnson, Rohnert Park, all of Calif.

[73] Assignee: Henkel Research Corporation, Santa Rosa, Calif.

[21] Appl. No.: 540,037

[22] Filed: Jun. 19, 1990

[51] Int. Cl.$^5$ ............................................ C07D 233/58
[52] U.S. Cl. .................................................... 548/335
[58] Field of Search ....................................... 548/335

[56] References Cited
U.S. PATENT DOCUMENTS 4,062,965  12/1977  Holtschmidt et al. .............. 548/335
4,301,170  11/1981  Houlihan ............................ 548/335

Primary Examiner—Robert W. Ramsuer
Assistant Examiner—Patricia L. Morris
Attorney, Agent, or Firm—Ernest G. Szoke; Wayne C. Jaeschke; John E. Drach

[57] ABSTRACT

Imidazoles are alkylated at the 1-position by adding an alkyl halide a mixture comprising an imidazole, a non-reactive aromatic solvent and a base at temperature of from about 75° C. to about 115° C. and then maintaining the temperature for a period of time sufficient to produce the 1-alkylimidazole and then separating any inorganic material from the product.

9 Claims, No Drawings

PROCESS FOR PREPARING 1-ALKYLIMIDAZOLES

BACKGROUND OF THE INVENTION

1. Field of the Invention

This invention relates to a process for preparing 1-alkylimidazoles of high purity and in high yield.

2. Description of the Related Art

The alkylation of imidazoles at the 1-position by reaction with an alkyl halide is known in the prior art. U.S. Pat. No. 4,140,518 teaches that 2-alkyl imidazoles can be alkylated at the 1-position by reacting the imidazole and a 10% molar excess of alkyl halide in the presence of sodium hydroxide. The alkyl halide and imidazole are heated to 130° C. for 30 minutes whereupon the sodium hydroxide is added and the temperature is then increased to 150° C. and held there for 2 hours. The patent also teaches that the alkylation reaction can be accomplished in an inert, organic diluent which is preferably dimethylformamide. U.S. Pat. Nos. 4,525,475 and 4,328,234 teach that imidazoles can be alkylated at the 1-position using alkyl halide and an acid acceptor such as an alkali metal alkoxide in the absence of solvent. U.S. Pat. No. 4,282,238 teaches that imidazoles can be alkylated at the 1-position by reacting 1 mole of an alkyl halide with 2 moles of imidazole in such solvents as tetrahydrofuran and dioxane at 160° C. for 15 hours in the absence of base and solvent. European Patent Application 0,066,884 teaches that 1-lauryl-2-methylimidazole can be made by heating 0.23 moles of 2-methylimidazole and 0.10 moles of lauryl bromide at 200° C. for 10 hours in the absence of inorganic base and in the absence of solvent. Chemical Abstracts 70:11699f teaches that 1-dodecyl-2-methylimidazole can be made by dropping 1 mole of dodecyl chloride into a mixture comprised of 1 mole of 2-methylimidazole and 1 mole of sodium hydroxide at 140°–150° C. in the absence of solvent. Chemical Abstracts 89:109246y teaches that 1-alkylimidazoles can be prepared by adding the imidazole in tetrahydrofuran solution to a suspension of sodium hydride or t-butyl alcohol in tetrahydrofuran, refluxing for 4 hours, cooling, adding an alkyl halide, and refluxing for an additional 6 hours. Biochemical Pharmacology 23, 2377–2386 (1974) teaches that 1-hexylimidazole can be prepared in 68% yield by heating a mixture comprising 0.1 moles of imidazole and 0.12 moles of n-hexylbromide to reflux for 1 hour. The Journal of The American Chemical Society 93, 6584 (1971) teaches that 1-dodecylimidazole can be prepared by heating a mixture comprising equimolar quantities of imidazole and lauryl bromide at 150° C. for 1 hour in the absence of base in the absence of solvent.

The reaction of imidazoles and alkyl halides is generally disclosed in U.S. Pat. No. 3,507,831 and in Chemical Abstracts 99:88113s, 91:157734u, 91:74616f, 82:4255c, 69:106622u.

The reaction of imidazoles and alkyl halides in the presence of phase transfer catalysts is generally disclosed in Chemical Abstracts 109:230887t, 102:131300v, 101:6977z, 99:87391u, 99:69862u, and 87:5864r. British Patent 1,122,717 teaches the alkylation of imidazoles with a molar excess of alkyl halide and a large excess of base in the presence of polar solvents such as alcohols or ketones which are at least partially water soluble. The use of these partially water soluble solvents leads to difficulties in an aqueous work up step which removes the excess base. British Patent 1,122,717 also teaches that no product is obtained from the attempted alkylation of imidazoles in non-polar solvents like toluene even in the presence of excess alkyl halide. Other disadvantages with the prior art processes include low product purity, poor yields, solvent losses during aqueous work up, and product purification steps. Contrary to the teachings of British Patent 1,122,717, surprisingly high yields of very pure product containing only small amounts of the 3-alkyl quaternary ammonium compound can be obtained by alkylating imidazoles in aromatic solvents when the alkyl halide is present in less than a 1:1 molar ratio of imidazole:alkyl halide.

None of the prior art processes combines the steps of the gradual addition of an alkyl halide to a slight molar excess of imidazole in a non-reactive aromatic solvent at temperatures of about 115° C. or below. None of the prior art processes is conducive to scale up to a commercial process because they involve carrying out the reaction in the absence of solvent and/or carrying out the reaction at temperatures greater than 115° C. or carrying out the reaction in solvents with unacceptable water solubilities. Many of the processes of the prior art produce a product containing unacceptable amounts of the quaternary ammonium product produced by double alkylation. The process of the present invention eliminates the problems encountered by the prior art processes by carrying out the reaction in non-polar solvents such as toluene or other non-reactive aromatic solvents using a deficiency of alkyl halide at a temperature of about 90° C. Inorganic materials dissolved in the reaction solvent can be conveniently and easily extracted with water leaving a solution of substantially pure 1-alkylimidazole.

SUMMARY OF THE INVENTION

The present invention provides a process for preparing a 1-alkylimidazole comprising the steps of: (1) heating a mixture comprised of an imidazole, a base, and a non-reactive aromatic solvent to a temperature of from about 75° C. to about 115° C.; (2) adding to said heated mixture from about 0.8 to about 1.0 moles of an alkyl halide per mole of said imidazole over a period of from about 1 hr to about 5 hours to produce a reaction mixture; (3) maintaining the temperature of said reaction mixture for period of time sufficient to produce a product mixture comprising a solution of said 1-alkylimidazole in said solvent and inorganic material; and, (4) separating said inorganic material from said solution.

DESCRIPTION OF THE PREFERRED EMBODIMENTS

The present invention provides a process for the preparation of 1-alkylimidazoles comprising the steps of: (1) heating a mixture comprised of an imidazole, a base, and a non-reactive aromatic solvent to a temperature of from about 75° C. to about 115° C.; (2) adding to said heated mixture from about 0.8 to about 1.0 moles of an alkyl halide per mole of said imidazole over a period of from about 1 hr to about 5 hours to produce a reaction mixture; (3) maintaining the temperature of said reaction mixture for period of time sufficient to produce a product mixture comprising a solution of said 1-alkylimidazole in said solvent and inorganic material; and, (4) separating said inorganic material from said solution.

The process is carried out by heating a mixture comprised of an imidazole, a base, and a non-reactive aromatic solvent to a temperature of from about 75° C. to about 115° C. For purposes of this invention, a non-reactive aromatic solvent is an aromatic hydrocarbon having a boiling point in the range of 75° C. to 200° C. or an aromatic compound having one or more functional groups which do not interfere in the reaction such as the ether functionality having a boiling point in the range of 75° C. to 200° C. Functional groups which can interfere in the reaction are those which are nucleophilic such as —OH, O−, —NH$_2$, —NR$_2$, —SH, —S−, —COO−, —COOH, etc. Other functional groups which do not interfere in the alkylation reaction will be recognizable to those skilled in the art. Examples of aromatic solvents contemplated by this invention include but are not limited to such aromatic hydrocarbon solvents as benzene, toluene, xylene and such functionalized aromatic solvents as diphenyl ether and anisole. The preferred solvents are benzene, toluene, xylene. The most preferred solvent is toluene. Another desirable characteristic of the solvents discussed above is their low solubility in water which allows step (4) of the present invention to be carried out by water extraction of dissolved inorganic materials disclosed below from the reaction product mixture at the end of the reaction.

It is understood that the present invention also contemplates the use of mixtures of non-reactive aromatic solvents as well as solvent systems comprised of non-reactive aromatic solvents and other types of solvents such as alcohols, aldehydes, ketones, esters, liquid N,N-dialkylamides, and sulfoxides and the like which are present in quantities which do not substantially alter the water solubility of such solvent mixtures and thereby adversely affect the removal of the inorganic material from the final reaction mixture when step (4) is accomplished by water extraction.

Any imidazole which is unsubstituted at the 1-position can be used in the process of the present invention. The process of the present invention is particularly useful in preparing imidazoles of the formula I.

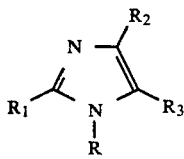

I wherein R is a C$_{8-24}$ alkyl group, R$_1$ is hydrogen or a C$_{1-24}$ alkyl group, R$_2$ is hydrogen or a C$_{1-6}$ alkyl group, R$_3$ is hydrogen or a C$_{1-6}$ alkyl group.

The base can be an alkali metal hydroxide, alkaline earth metal hydroxide, or an alkali metal carbonate. The preferred base is alkali metal hydroxide or an alkaline earth metal hydroxide. The most preferred base is potassium hydroxide.

The molar ratio of imidazole to base in the first step of the process of the present invention can vary from about 1:0.9 to about 1:1.5.

The alkylation reaction is carried out at a temperature of from about 75° C. to about 115° C. Temperatures lower than 75° C. lead to the production of unacceptable amounts of side product while temperatures greater than 115° C. do not significantly increase the yield of 1-alkylimidazole.

The alkyl halide is added over a period of from about 1 hour to about 5 hours with the optimum time period being from about 3 to about 4 hours. After all of the alkyl halide has been added, the reaction mixture is maintained at a temperature of at least 75° C. until the imidazole has been alkylated. The course of the alkylation is monitored by gas chromatographic analysis of the reaction mixture for the presence of unalkylated imidazole or of alkyl halide (gas chromatographic conditions are given in Example 2).

After the reaction is completed, the reaction mixture contains a solution comprised of the 1-alkylimidazole and inorganic materials dissolved in the non-reactive aromatic solvent. The dissolved inorganic materials are unreacted base and inorganic salts which would be expected to form in the alkylation reaction. In addition, substantial amounts of insoluble unreacted base and inorganic salt are dispersed in the solution. For example, if imidazole is alkylated with 1-bromobutane in the presence of potassium hydroxide in toluene, the product mixture would contain a 1-butylimidazole-toluene solution in which are dissolved small amounts of potassium bromide and unreacted potassium hydroxide and undissolved potassium bromide and potassium hydroxide dispersed in the 1-butylimidazole-toluene solution. The solid inorganic material can be separated from the toluene solution by any means known to those skilled in the art such as by filtration. Inorganic material as defined above dissolved in the toluene solution can be removed by any means known to those skilled art such as by washing the organic phase with aqueous brine solutions. The imidazole product may be isolated from the solvent or may remain dissolved therein. The product imidazole can be isolated by any means known to those skilled in the art such as by distillation of the solvent. In a preferred embodiment of the present invention, about 1.5 moles of 2-methylimidazole and about 1.9 moles of potassium hydroxide powder are mixed with about 536 mL of toluene and heated to about 60° C. for 30 minutes with stirring. The temperature is then raised to 90° C. and about 1.36 moles of 1-bromododecane are added over 60 minutes. After the addition is complete, the reaction mixture is then maintained at 90° C. until the 1-bromododecane is no longer observable by GC analysis of the reaction mixture. The reaction mixture is then cooled and the organic phase and inorganic phases separated by filtration. The organic phase is washed with four 500 mL portions of brine and the toluene is removed at 40° C. under vacuum leaving a 99 mole % yield of N-dodecyl-2-methylimidazole relative to 1-bromododecane.

The following examples serve to illustrate but not limit the invention.

EXAMPLE 1

About 124 g of 2-methylimidazole (1.5 moles) and 106 g of potassium hydroxide powder (1.89 moles) were introduced into a 2-liter glass reaction vessel containing 536 mL of toluene (465 g). The reaction flask was equipped with a nitrogen inlet to blanket the reaction mixture and an overhead stirrer. The reaction temperature was initially set at 60° C. for 30 minutes with stirring to dissolve a portion of the imidazole. After this time the reaction temperature was raised to 90° C. and 326 mL of 1-bromododecane (1.36 moles) was added over 60 minutes using a dropping funnel. After the addition was complete, the reaction mixture was heated for another 3.5 hours at 90° C. Heating was then discontinued, and the organic phase was washed with four 500 mL portions of brine. 15 mL of isopropanol was added to the first wash to induce separation. The pH of the final aqueous wash was 8-9. The toluene was then removed at 40° C. under vacuum. The resulting N-dodecyl-2-methylimidazole was a rust-colored liquid, b.p. (760 mm Hg) 380° C., $n^{24}{}_D = 1.4721$. Concentration of N-dodecyl-2-methylimidazole relative to 1-bromododecane: 99 Mol % (H-NMR); purity 97% (GC area %).

EXAMPLE 2

Using a procedure similar to example 1, 23.1 g of 2-methylimidazole (0.28 moles) and 23.6g of potassium hydroxide powder (0.42 moles) were introduced into a 250 mL glass reaction vessel containing 107 mL toluene (93 g). After reacting this mixture at 60° C. for 30 minutes the temperature was increased to 90° C., and 67 mL of 1-bromododecane (0.28 moles) was added at the rate of 1.26 mL/min using a syringe pump. After a reaction time of 4.5 hours (including the 1-bromododecane addition time), heating was discontinued. The organic phase was washed as before with a saturated brine solution until the pH of the aqueous was 8-9, and the toluene was removed at 40° C. under vacuum. The resulting N-dodecyl-2-methylimidazole had the same physical and chemical characteristics as the product of example 1. Yield of N-dodecyl-2-methylimidazole, relative to 1-bromododecane: 99 Mol % (H-NMR), purity 99% (GC area %). GC analyses were carried out with a 25m HP-5 capillary column with an initial column temperature of 60° C., increasing after 1 minute at 25° C./min. to 300° C. and then holding for 5 minutes. $^1$H-NMR of the product showed only the following peaks ($\tau$ values): 0.89 (3H, t, term. CH$_3$); 1.26 (18H, s, methylenes), 1.7 (2H, m, $\beta$-CH$_2$); 2.31 (3H, s, 2-CH$_3$); 3.80 (2H, t, $\alpha$-CH$_2$); 6.80 (2H, s, vinyl H).

EXAMPLES 3-4

In substantially the same manner as described in example 2, 0.5 mole of 2-Methylimidazole and 0.5 mole of Potassium hydroxide powder were reacted with 0.5 mole of 1-bromododecane in 50 mL of n-amyl alcohol (40.8 g), or 50 mL of tert-amyl alcohol (40.8 g), representing examples 3 and 4, respectively. The results of these examples are shown in Table I

TABLE I

| Example | Solvent | Reaction Time (hours) | Temperature (°C.) | % Purity |
|---|---|---|---|---|
| 1 | Toluene | 4.5 | 90 | 99 |
| 2 | Toluene | 4.5 | 90 | 99 |
| 3 | n-amyl alcohol | 4.5 | 90 | 77 |
| 4 | tert-amyl alcohol | 4.5 | 90 | 76 |

COMPARATIVE EXAMPLES

The following examples illustrate the effect on the yield of 1-alkylimidazole product when a diluent suggested in column 2, lines 34-35 of U.S. Pat. No. 4,140,518 is employed in the procedure disclosed in Example 1 of U.S. Pat. No. 4,140,518.

COMPARATIVE EXAMPLE 1.

21.0 g of 2-methylimidazole (0.26 moles) and 71.6 g of 1-bromododecane (0.29 moles) were introduced into a 300 mL glass reaction vessel containing 107 mL of mixed xylene isomers (93 g). The reaction flask was equipped with a slow nitrogen inlet stream to blanket the reaction mixture and an overhead stirrer and reflux condenser. The reagents were heated to reflux for 30 minutes with stirring, and then 23.5 g of powdered potassium hydroxide (0.42 moles) was slowly added. A sudden exotherm occurred, causing the reactor contents to overflow the reaction vessel. The reaction was stopped.

COMPARATIVE EXAMPLE 2

The procedure of comparative example 1 was repeated except that the glass reaction vessel was 500 mL and the potassium hydroxide was charged into the reactor in 10 equal portions over 15-30 minutes to prevent overflow. An exotherm still occurred but not as violently. After the addition of the base, the reaction was allowed to react for two hours at reflux (temperature=137° C.-144° C.) before removing the heat source. At this time the liquid was filtered and xylene removed at 40° C. under vacuum. The resulting product was a rust colored liquid. The yield by GC was 76% (area %). Qualitative analysis by $^1$H-NMR indicated a purity of 50-60 mol % N-dodecyl-2-methylimidazole, plus significant alkyl halide decomposition products, and production of at least two unknown components accounting for an estimated 30 mol %.

What is claimed is:

1. A process for preparing a 1-alkylimidazole comprising the steps of: (1) heating a mixture comprised of an imidazole, a base, and a non-reactive aromatic solvent to a temperature of from about 75° C. to about 115° C.; (2) adding to said heated mixture from about 0.8 to about 1.0 moles of an alkyl halide per mole of said imidazole over a period of from about 1 hr to about 5 hours to produce a reaction mixture; (3) maintaining the temperature of said reaction mixture for period of time sufficient to produce a product mixture comprising a solution of said 1-alkylimidazole in said solvent and inorganic material; and, (4) separating said inorganic material from said solution.

2. The process of claim 1 wherein said alkyl halide is added to said reaction mixture over a time period of from about 3 to about 4 hours.

3. The process of claim 1 wherein said alkyl halide is 1-bromododecane.

4. The process of claim 1 wherein said base is an alkali metal hydroxide.

5. The process of claim 4 wherein said alkali metal hydroxide is potassium hydroxide.

6. The process of claim 1 wherein said aromatic solvent is toluene.

7. The process of claim 1 wherein said 1-alkylimidazole is a compound of the formula I:

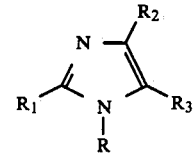

wherein R is a C$_{8-24}$ alkyl group, R$_1$ is hydrogen or a C$_{1-24}$ alkyl group, R$_2$ is hydrogen or a C$_{1-6}$ alkyl group, R$_3$ is hydrogen or a C$_{1-6}$ alkyl group.

8. The process of claim 7 wherein R is dodecyl, R$_1$ is methyl, and R$_2$ and R$_3$ are hydrogen.

9. The process of claim 7 wherein R is dodecyl, and R$_1$, R$_2$, and R$_3$ are hydrogen.

* * * * *